US 6,647,089 B1

(12) United States Patent
Virta et al.

(10) Patent No.: US 6,647,089 B1
(45) Date of Patent: Nov. 11, 2003

(54) METHOD AND APPARATUS FOR TISSUE IMAGING

(75) Inventors: Arto Virta, Helsinki (FI); Jan Fröjdman, Söderkulla (FI); Timo Sulin-Saaristo, Helsinki (FI); Jorma Jänkävaara, Järvenpää (FI)

(73) Assignee: Planmed Oy, Helsinki (FI)

( * ) Notice: Subject to any disclaimer, the term of this patent is extended or adjusted under 35 U.S.C. 154(b) by 0 days.

(21) Appl. No.: 09/856,800

(22) PCT Filed: Nov. 29, 1999

(86) PCT No.: PCT/FI99/00988

§ 371 (c)(1),
(2), (4) Date: Aug. 2, 2001

(87) PCT Pub. No.: WO00/32109

PCT Pub. Date: Jun. 8, 2000

(30) Foreign Application Priority Data

Nov. 27, 1998  (FI) .................................................. 982580

(51) Int. Cl.⁷ ................................................ A61B 6/04
(52) U.S. Cl. ........................................................ 378/37
(58) Field of Search ............................... 378/37, 51, 62, 378/63, 86, 87, 88, 89

(56) References Cited

U.S. PATENT DOCUMENTS

| 4,122,587 | A | * | 10/1978 | Weiss et al. ................... 5/621 |
| 4,143,445 | A | * | 3/1979 | Fougman .................... 24/68 R |
| 5,553,111 | A | * | 9/1996 | Moore et al. ................. 378/37 |
| 5,851,180 | A | * | 12/1998 | Crosby et al. .............. 600/407 |

* cited by examiner

Primary Examiner—Eric S. McCall
(74) Attorney, Agent, or Firm—Steinberg & Raskin, P.C.

(57) ABSTRACT

The object of the invention is a method and apparatuses used in tissue imaging, in particular for positioning the tissue to be imaged in the imaging area. For example, in mammography the tissue has generally been, among other things, compressed with compression plates and/or even physically pulled into the imaging area. In accordance with the invention, a tissue stretching solution is presented, whereby a tissue stretching means, which comprises a layer of flexible material that is translucent to the energy form, containing image information, used in imaging, is simply, quickly and effortlessly feedable and attachable to the tissue stretching device.

45 Claims, 5 Drawing Sheets

2a

2b

2c

2d

METHOD AND APPARATUS FOR TISSUE IMAGING

FIELD OF THE INVENTION

This invention relates to a method and apparatuses for tissue imaging, especially for positioning tissue within the imaging space.

BACKGROUND OF THE INVENTION

Various positioning methods are utilized for example in mammography, where it is known e.g. to compress the tissue to be imaged between compression plates and/or even to physically pull within the imaging space.

Currently, there is a multitude of known technologies used for tissue imaging, such as, for example x-ray, ultrasound, and magnetic imaging technologies. Imaging has become a proven method for the detection of e.g. cancers and other abnormalities before they advance to a phase that is difficult to treat or incurable.

One of the problem areas associated with the imaging of tissue involves the positioning and retaining of tissue within the imaging space during the imaging process. The more successful one is in positioning of the tissue within the imaging space, the less probable is the need for subsequent exposures in place for the unsuccessful ones. Problems encountered in positioning may also result in more images of a tissue area becoming taken than would be absolutely necessary. These problems are emphasized when x-rays are used, in which case the importance of radiation hygiene, i.e. the need to minimize exposure of the tissue to radiation, must always be taken into consideration.

One of the methods utilized for the positioning of tissue, especially in mammography, is compression of the tissue to be imaged. The main reason for compressing tissue is to keep it in place during the imaging process. However, when the tissue layer to be imaged gets thinner, the amount of radiation also gets smaller and the imaging time is shortened, which further reduces the inaccuracies caused by movement of the tissue under exposure. Furthermore, as a result of a thinner layer of tissue the contrast of the image improves as scattering is reduced, which simultaneously enables the use of lower imaging values (kV). Additionally, resolution improves, the film darkens more homogeneously, and the result is a diagnostically more valuable image, since possible deviations of superimposed tissue layers are more effectively differentiated from each other.

In mammography, areas easily excluded from the imaging space are those close to the chest wall and armpits, where cancers and tissue abnormalities quite often occur. On the other hand, the process of compression can even lead to part of the tissue under exposure being pushed out of the imaging space. Therefore, efforts have been made in this field to develop various solutions related to compression plates and compression methods that would make it possible to pull or otherwise manipulate the tissue of the chest and breast areas in such a fashion that the imaging space created by the compression plates would retain as much tissue as possible. Even negative pressure has been used in an attempt to draw tissue into the imaging space by suction.

A rather new and interesting method for drawing the breast into the imaging space has been presented in U.S. Pat. publication No. 5,553,111. According to this procedure, a layer of radiolucent material is positioned between the compression plate and the tissue to be imaged, for instance a layer of plastic film. This film is positioned between the tissue to be imaged and the contact or compression surfaces of the compression plates, for example so that the film passes both over and under the breast. Thereafter, the film is pulled in the direction of the tip of the breast in order to pull more tissue within the imaging space. The publication proposes utilizing either one continuous layer of film to pull tissue from opposite sides, or separate bands of film that are fastened at both ends to their individual film conveyors in order to create substantially a ring-shaped stretching means, which passes around the compression paddle used for compressing the tissue to be imaged.

In principle, the technology described in U.S. Pat. publication No. 5,553,111 contains many advantageous features. However, in a practical application of these principles the solutions presented are in many respects problematic. Because. of the modern demand for strict hygiene, among other things, it would be advisable to change the disposable film or the corresponding stretching means for every client. The solutions specified in the patent publication for pulling the film, and for fastening it to the traction device, etc., do not include a means for quickly changing the stretching means between customers. In addition, in the solutions presented, sanitizing the traction device in situ would be awkward and uncertain. For example, in mammography screening tests, the time factor is of such importance that it would appear that the technology described in the publication could not be utilized as such, except possibly for clinical imaging.

OBJECTS AND SUMMARY OF THE INVENTION

Therefore, the object of the invention presented here is to raise the level of technology in the field of positioning methods related to tissue imaging.

Specifically, the object of the invention presented herein is to develop the technology based on tissue stretching means so as to speed up the practical process of imaging.

The object of the invention is to provide a solution whereby the tissue stretching means could be simply, quickly and easily fed and fastened to a tissue pulling device, thereby resulting in a reduction of the total imaging time and eliminating difficult installation procedures.

The object of the invention is to provide a solution to feeding the stretching means into the traction device in such a way that a sheet-like stretching means, or stretching means of some other, in its principal dimensions essentially a rectangular configuration, could be fed into the traction device as easily as a bank card or a note is fed into an. automatic cash dispenser, or the like.

The object of the invention is also to provide a solution for fastening the tissue-stretching means to the tissue-stretching device so as to guarantee a rapid, secure and non-slip lockage of the stretching means to the traction device.

Moreover, the aim of the invention is to provide such a solution for fastening the stretching means to the traction device, as well as to provide such a traction device, that the stretching means can be both pulled into the device as well as driven out of it.

The object of the invention is also to provide an imaging system that utilizes tissue traction technology whereby the imaging methods and imaging sequences typically used in mammography can be applied simply, efficiently and, if so desired, to some degree automatically.

The aim of the invention is also to enable the utilization of all those components generally used in mammography, such as the various compression paddles, image information receivers, grids, etc., in the same fashion as before.

BRIEF DESCRIPTION OF THE DRAWINGS

The invention and some of its advantageous applications are described below by referring to the enclosed figures. However, the invention is not exclusively limited to these solutions but essential features of it are presented in the enclosed patent claims, specifically in the characterizing parts of the independent patent claims.

In the enclosed figures the invention is illustrated with reference to an x-ray application. To a professional in this field, it is self-evident which parts the structure of the ultrasound device adapted for the invention would deviate from the structure of the x-ray apparatus presented here, Of the enclosed figures

DETAILED DESCRIPTION OF THE INVENTION

Figure 1:
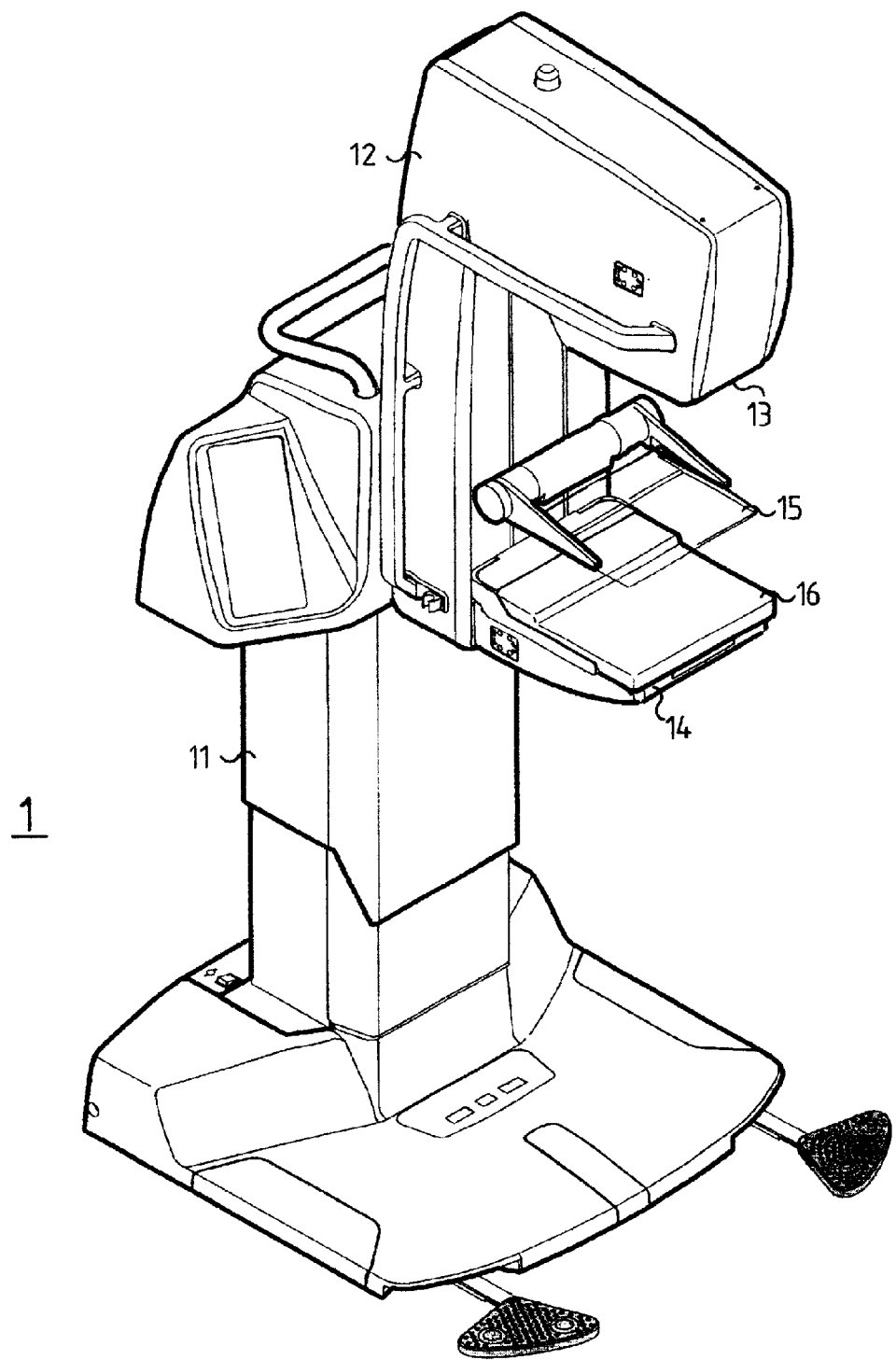
FIG. 1 depicts a mammography x-ray apparatus.

In accordance with FIG. 1, a typical mammography x-ray apparatus 1 comprises a body part 11 and a C-arm 12, or a corresponding part, connected to the body part 11, when typically a radiation source 13 and a radiation receiver 14 (not actually shown in the figure) are situated at the opposite ends of the C-arm 12. Typically, C-arm 12 can be moved vertically and rotated in relation to the body part 11. Moreover, it is typical for compression paddles 15, 16 to be used in the apparatus, one of which is often structurally attached to the radiation receiver 14. The apparatus is typically equipped with means (not shown in the figure) for changing the height position of the compression paddles 15, 16 in relation to C-arm 12.

Figure 2:
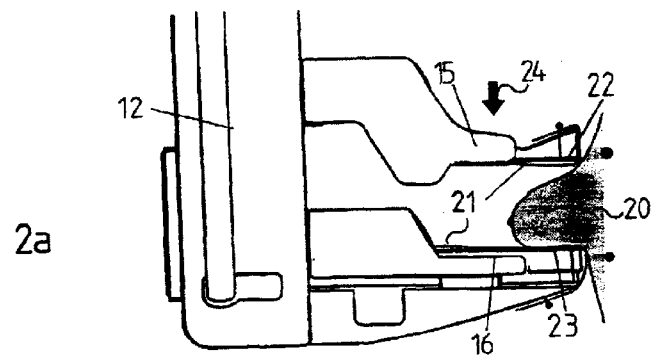
FIG. 2 depicts the general principle of the traction of tissue to be imaged in accordance with typical prior art technology.
Figure 2:
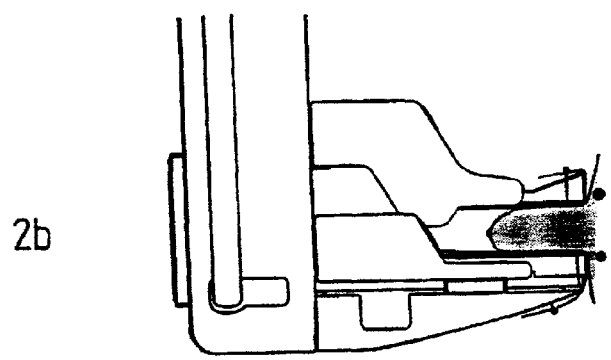
Figure 2:
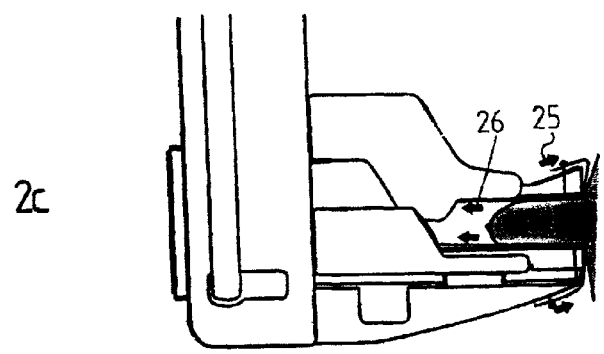
Figure 2:
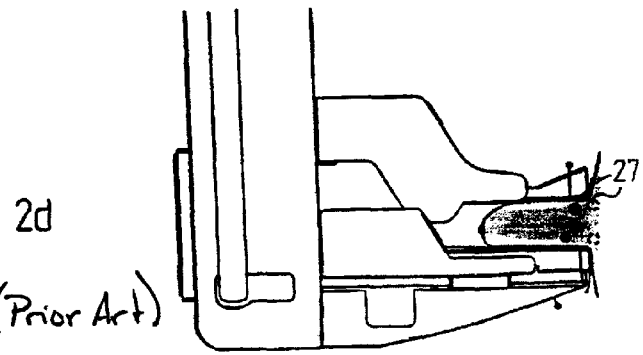

FIG. 2 depicts the general principle for traction of the tissue to be imaged in accordance with prior art in connection with a mammography apparatus utilizing compression technology. In this respect, it is emphasised that although compression is a beneficial method from the viewpoint of applying the invention, the mere contact of the compression paddles with the stretching means and through it to the tissue to be imaged could in some applications of the invention be sufficient.

Before positioning the tissue to be imaged 20 in the imaging space created between the compression paddles 15, 16, a stretching means 21 made of elastic material is installed in the imaging device in accordance with FIG. 2. In accordance with the prior art, stretching means 21 can comprise, for example, a continuous band of film that is positioned to move along the contact or compression surfaces 22, 23 of compression paddles 15, 16 and through the traction device not shown in the figure. The traction device can be situated, for example, within the C-arm 12, in which case it is equipped with means for pulling the stretching means 21 approximately from its center towards the C-arm 12. In this case, the tissue to be imaged 20 could be placed in the pouch-shaped space open at the sides created by the stretching means 21. Alternatively, in accordance with prior art, the stretching device could comprise a ring-shaped stretching means 21 moving around either one or the other or around both individual compression paddles 15, 16, as well as being comprised of a transport device for either of such stretching means 21.

In accordance with FIG. 2, the tissue imaging process is initiated by moving, for example, the upper compression paddle 15 towards the lower compression paddle 16 (2a), such that the tissue to be imaged 20 gets evenly spread out: over the imaging space (2b). The traction of tissue 20 within the imaging space is initiated by starting up the traction device or a separate conveyor device, not shown in the figure, which moves 25 the stretching means 21 in relation to the contact or compression surfaces 22, 23, whereby the tissue to be imaged 20 starts stretching in the direction of traction 26 and tissue located outside the space of contact or compression surfaces 22, 23 starts moving towards the imaging space (2c). Thus the image to be taken of tissue 20 will comprise such tissue that would normally remain outside the imaging space and where lesions 27 often occur (2d). The amount of the movement of tissue does not have to be at all large. For example, the transfer of a few millimeters can already be diagnostically significant.

Figure 3:
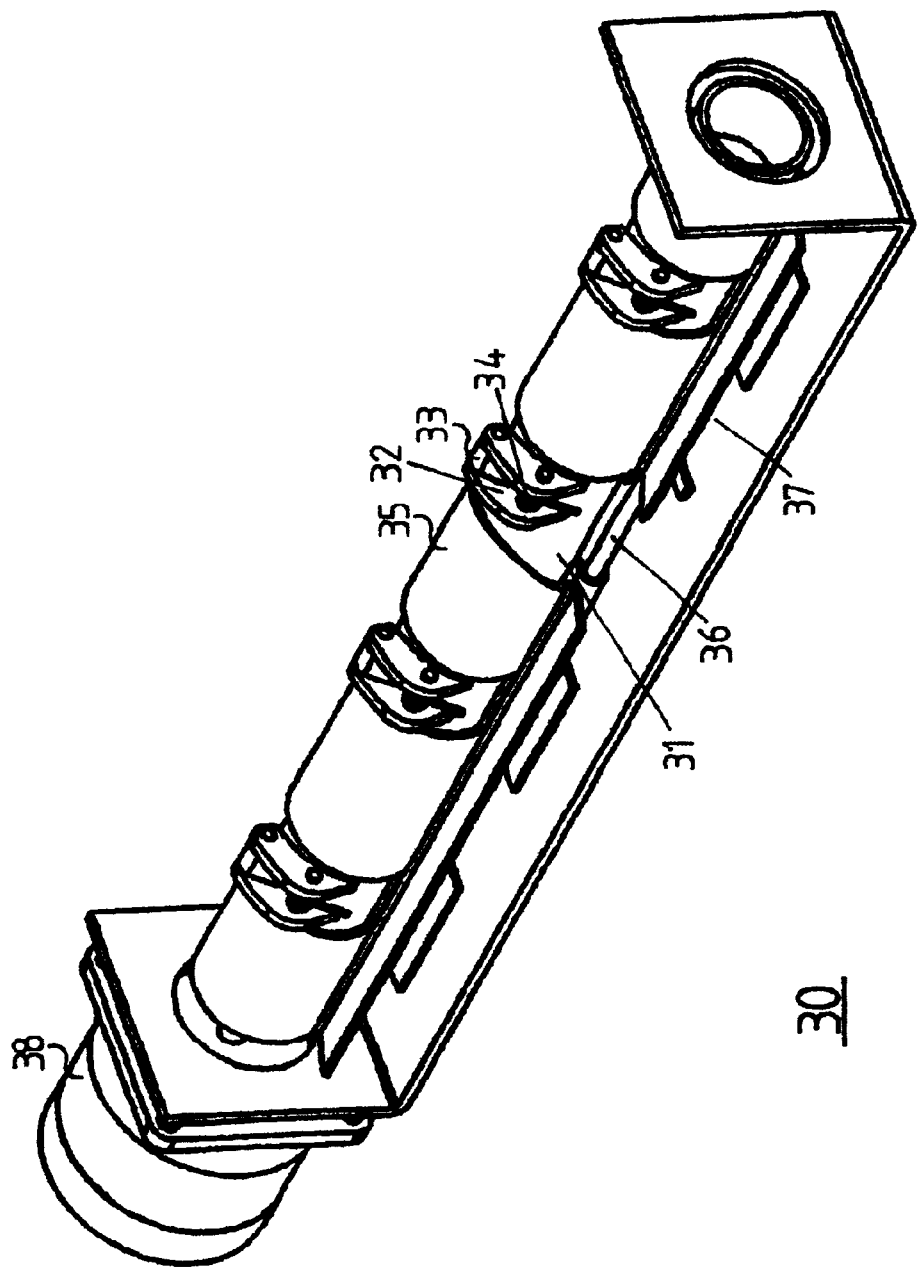
FIG. 3 depicts one stretching device according to the invention.

FIG. 3 depicts one traction device 30 according to the invention that comprises a, rotating axle, cylinder or drum 31, one or several means 32 for locking the stretching means 21, the operating part of which consists of, e.g., an eccentric wedge 33, a compressor spring 34 of the eccentric wedge 33, one or several guides 35 for the stretching means, and the release bar 36 of the eccentric wedge 33 or a corresponding component. Furthermore, the stretching device may comprise a receiver means for the stretching means, in FIG. 3 a wedge-shaped aperture 37 of the guide 35 of the stretching means 21. A motor 38 and power transmission means, not shown in the figure, drive the stretching device 30.

FIGS. 4a–c describe the functioning of the stretching device 30 as shown in FIG. 3. Stretching means 21, which is made of elastic material .and is advantageously substantially rectangular in shape, is fed into the wedge-shaped receiving aperture 37 that directs stretching means 21 into a position between the cylinder 31, which can be rotated, and the eccentric wedge 33 (4a). The compressor spring 34 of the eccentric wedge 33 assists the engagement of the stretching means 21 between the wedge 33 and the cylinder 31, but the actual locking is based on the structure of the eccentric wedge 33 itself and the fixation of it to the stretching device 30. The eccentric wedge 33 tends to continuously adhere itself more closely to the cylinder 31, when the stretching means 21 that is fed into the space between the cylinder 31 and the eccentric wedge 33 is exposed to a force from the direction that extracts it from device 30. The stretching means 21 is pulled by the rotating cylinder 31. The dimensions and gear ratios between the stretching device 30 and the power transmission means can be such, for example, that rotation of cylinder 31 for half a cycle is sufficient to pull stretching means 21 to the supposed maximum distance, for example 50 mm (4b). Stretching means 21 is disengaged by rotating cylinder 31 in the opposite direction, whereby the sheath-like guide 35 that covers cylinder 31 feeds stretching means 21 from device 30 and the lock of stretching means 21 is released when the eccentric wedge 33 comes into contact with the release bar 36 that turns the eccentric wedge 33 so that it disconnects with the surface of the cylinder 31 (4c).

Stretching device 30 may also comprise means, not shown in the figures, for identification of the feeding of the stretching means 21. For example, in connection with compressor spring 34 a micro switch can be installed that would react when coming into contact with stretching means 21. Alternatively, guide 35 can be equipped with components for the optical identification of the stretching means 21. Identification can also be specifically arranged so that the type of stretching means 21 fed into device 30 can be identified. In such case the control system may include a signal route from identification means to traction or transport means, and the control system may be pre-programmed with typical imaging process parameters for each stretching means, Stretching device 30 can contain e.g. automatic control systems for locking the stretching means 21 based on an identification signal, e.g. by rotating cylinder 31 according to FIGS. 3 and 4 or a corresponding device, a short distance. If desired, the whole imaging process can be automated according to the pre-programmed parameters of the apparatus, among other things when the compression ceases, the stretching means can be fed out of the device either to its initial position of imaging process, or entirely out of the device.

The arrangement can also comprise identification means for the traction force and traction distance of stretching means 21. In accordance with the invention, it is possible to arrange several stretching devices 30 that can be controlled independently of each other, thus making it possible to drive them, if so desired, by stretching the tissue only on one side or by stretching it from different sides for distances of variable length and/or by stretching tissue from different sides at different speeds. Device 30 can also be programmed to encompass different traction sequences or traction-related security limit values such as, for example, the maximum traction force of the stretching means and/or limit values of the maximum stretching length, which can amount to e.g. 300 N for the traction force, 50 mm for the stretching length and 20 mm/s for the stretching speed, whereby typical values in use would be somewhat lower than these limit values.

Naturally, the traction components of stretching device 30 do not have to comply in all their details with the above-mentioned advantageous embodiments. The locking of stretching means 21 to the stretching device can also be implemented in other ways, for example with a locking device attached to some sort of gliding cradle. Thus one advantageous way of implementing the stretching movement would be to move the cradle along a suitable groove, or corresponding element for controlling movement, advantageously in a linear fashion. It is also possible to utilize a solution whereby the traction means consists of two substantially parallel axles; both equipped essentially at their ends with intermeshing groove, gear or corresponding structures. During rotation such axles fasten the stretching means between the axles by said intermeshing grooves or corresponding means, which axles while rotating further convey the stretching means through the transport device. Such a solution is especially advantageous, when one seeks to draw out the stretching means from the imaging device by other than the feeding route.

Figure 5:
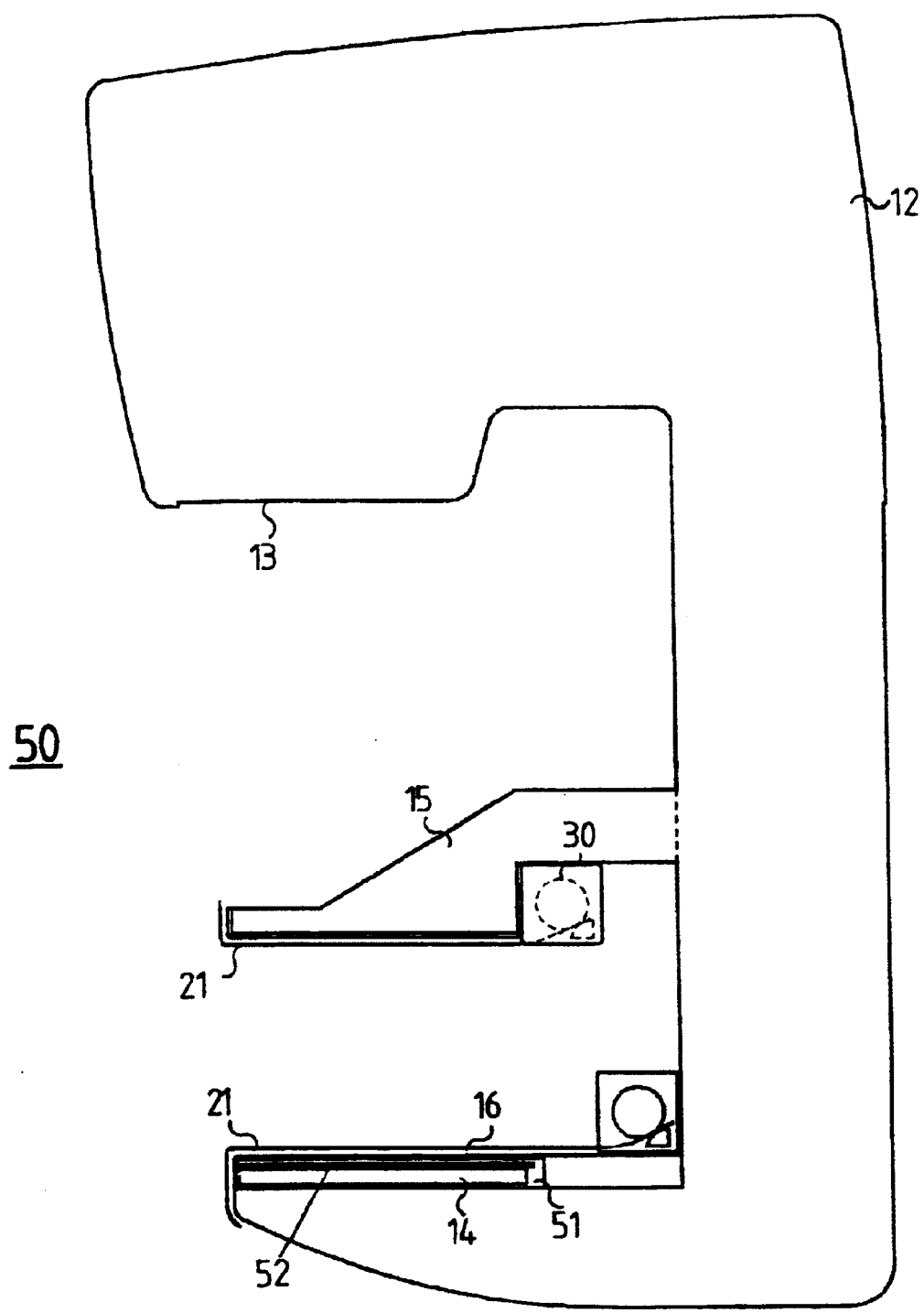
FIG. 5 shows an arrangement, according to the invention, of the stretching device for tissue to be imaged.

FIG. 5 shows how a stretching device 30, in accordance with the invention, can be integrated, for example, in a C-arm structure 12 typical to a mammography apparatus 1 in order to form a tissue positioning apparatus 50 according to the invention. In the arrangement shown in FIG. 5, the C-arm 12 includes the upper and lower compression paddles 15, 16, which are movable in relation to the C-arm, a cassette tunnel 51 coupled to the lower compression paddle 16, a movable grid 52, the so-called bucky, and the upper and lower stretching devices 30 in an essential vicinity of the compression paddles. A radiation receiver 14 of the desired type can be attached to the cassette tunnel 51, while the radiation source 13 is located on the opposite frame of the C-arm structure 12.

Figure 4:
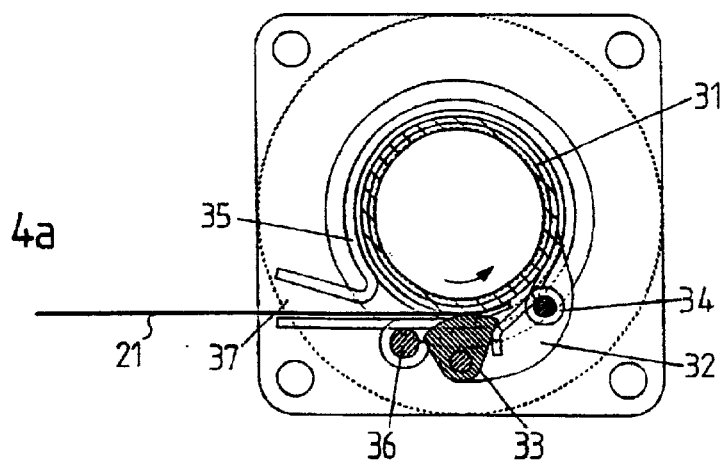
FIGS. 4a–c depicts the operation of a stretching device as specified in FIG. 3
Figure 4:
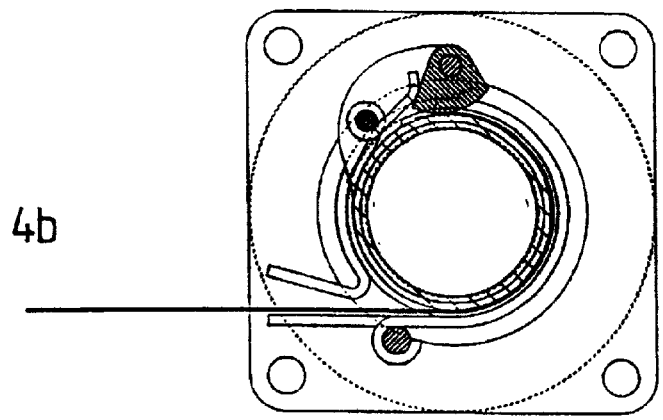
Figure 4:
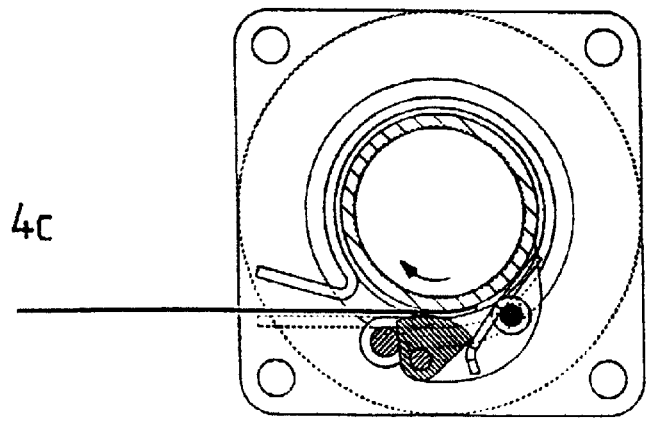

In the arrangement depicted in FIG. 5, it is possible to position a stretching means 21 for both of the compression paddles 15, 16 by engaging them, for example, to the stretching devices 30 shown in FIG. 3 and 4. Otherwise, the imaging process can be executed, for example, in the way referred to in the description which refers to FIG. 2.

On the other hand, one advantageous way to execute the imaging process, according to the invention, as, for example, in an arrangement according to FIG. 5, consists of stages wherein two stretching means 21 are fed into stretching devices 30 of their own, are then locked or engaged to the traction or transportation means of the stretching device 30, and the tissue to be imaged 20 is alternately first compressed and then pulled, possibly several times if necessary, provided the patient's ability to tolerate pain does not restrict the process. Thereafter, the picture is taken, the compression is released and the stretching means 21 are moved to their starting position, i.e. to the position they were in when locked or engaged to the traction or transportation means, after which the same phases are repeated in order to take a picture of the same object, but from a different angle and/or e.g. taking an image of the same object but of a different place in the tissue, i.e., taking an image first of one breast or breast tissue and then taking an image of the other breast or breast tissue.

The imaging process can be speeded up by simultaneously making the compression and stretching movements, as well as their counter movements. This type of simultaneous stretching and compression method can also be automated as a function of the increase of compression force and the decrease of compression thickness. The optimal compression force and pulling-speed/pulling-distance interdependence for various tissue types to be imaged can be determined by clinical tests. The tissue type can be identified, for. example, by compression thickness and force, in which case e.g. a tissue with a great starting thickness, and with which a relatively small force is needed for compression, can be drawn in greater volume to the imaging area than a tissue with the opposite qualities. Automation can be done for example by first compressing for a short distance, e.g. until a specific compression force is reached, after which the tissue is both pulled and compressed and possibly separately pulled or compressed at the end.

When using the imaging technology, which makes possible a real-time or a near real-time imaging or allows for the movement of the tissue, it can be advantageous, in a diagnostic sense, to stretch the tissue while imaging.

One of the advantages of the technique according to the invention is that it makes it possible to use all of the imaging practices typically used in mammography without requiring any special arrangements due to the application of the invention. For example. it would be difficult to apply the magnification imaging typical in mammography to at least some of the prior art solutions, since the stretching device arrangement would make changing the distance between the receiver and the imaging area difficult or even impossible. A stretching device in accordance with the invention can also be attached to an existing mammography apparatus with relatively small alterations.

Breast tissues, in particular, vary considerably in terms of size. Because of this, in mammography there has generally been used image information receivers of different sizes, two compression plates of different sizes and types etc., for objects of different sizes. In the tissue stretching device of the arrangement according to the invention, the advantage is that it does not in any way limit the possibilities for utilization of these different size and/or otherwise different equipment. Image information can also be received in the same way as with all known techniques, such as on film or digitally.

Although the invention has been described above in connection with the use of two compression plates closing on tissue from opposite sides, it can also naturally be used in connection with applications using just one or more than two compression plates or with the compression structure surrounding the tissue being imaged. When utilizing several compression paddles, it is often beneficial that they are made to approach the tissue being imaged in an essentially symmetrical fashion.

In accordance with the invention, the stretching material itself can be of any flexible material that is translucent to the energy form utilized in imaging. Potential materials include e.g. various types of plastics, fabrics, cellulose-based materials and even appropriate metals. The stretching means can be made so that it comprises areas with varying tensile stress, thus making it possible to regulate the degree of stretching of tissue even in this manner.

Furthermore, it is not necessary that the actual form of the stretching means be that of a genuine rectangle. What is essential is that the stretching means can easily be fed into the stretching device from one end. However, from the point of view of locking the stretching means, it may be advantageous to design some kind of projection or projections at the feeding end of it, in order that the stretching device can easily grasp and lock the stretching means. Projections of this kind can e.g. be in the form of a rectangle or a triangle, either pointed or blunt, and they can form the whole group of projections covering the feeding end of the stretching means. The appropriate form of the feeding end can also be used as an implement according to which the stretching device specifically identifies the stretching means.

Identifying the stretching means can, of course, be based on many other characteristics as well, such as the colour of the stretching means, a colour sticker or a bar code attached to the stretching means.

The invention also makes it possible to optimize the form of the stretching means as well as its structure, such as it's length, width, thickness and material to be applicable with various compression paddles. For example, with the upper and lower compression paddles one can use a specific stretching means, one can use specific stretching means for compression paddles of differing widths, as well as a specific stretching means with various, so called spot-compression paddles etc.

The applications outlined above represent favourable and potential embodiments of the invention to which it is in no way intended to be limited. The following patent claims define the scope of the invention, within the idea according to which many details may vary.

What is claimed is:

1. An apparatus for imaging tissues, in particular an apparatus for imaging breast tissue and tissue of the breast area, which apparatus comprises:
    a body part (11),
    a source of energy (13) used in the tissue (20) imaging and
      a receiver (14) for an energy form, said receiver containing image information of the tissue to be imaged, received from the source of energy (13),
    a control system of the imaging apparatus (1) and
    a positioning apparatus (50) for the tissue to be imaged (20), which positioning apparatus (50) includes
      a contact or compression device (11, 15, 16) which includes one of
        a contact surface approaching the tissue to be imaged (20),
        a contact or compression surface (22, 23),
        a continuous contact or compression surface encircling the tissue to be imaged (20), and
      a stretching device (30) for the tissue to be imaged, which includes
        stretching means (21) including a layer of flexible material that is translucent to the energy form used in the imaging,
        a traction or transportation means of the stretching means,
        means (37) for receiving the stretching means (21), and
        means for engaging the stretching means (21) to the traction or transportation means of the stretching device (30), wherein means (37) for receiving the stretching means (21) have been arranged to receive one of a rectangular, elongated sheet like and band like stretching means (21) from a direction of one end side, or from a corresponding direction in view of the shape of the stretching means (21).

2. An imaging apparatus according to claim 1, further comprising:
    means for driving the stretching means (21) out of the imaging apparatus (1) through implements that are separate from the receiving means (37) of the stretching means (21).

3. An imaging apparatus according to claim 1, wherein the source of energy form (13) used in imaging the tissue (20) is an x-ray tube.

4. The apparatus for imaging tissues according to claim 1, further comprising one of:
    means to lock the stretching means (21) to the traction or transportation means from the side the stretching means (21) is adjusted to be fed into the stretching device (30), and
    means to engage the stretching means (21) to:the traction or transportation means at the sides adjacent to the side from which the stretching means (21) is adapted to be fed into the stretching device (30).

5. The apparatus for imaging tissues according to claim 1, wherein said means for receiving the stretching means (21) comprises:
    a guide or some other structure (37), which endeavors to guide the stretching means (21) fed into the stretching device (30) around one of a drum, cylinder, bar, pipe, and axle (31) belonging to the traction or transportation means.

6. The apparatus for imaging tissues according to claim 5, wherein the means to engage the stretching means (21) to the stretching device (30) comprises:
    a locking device (32) operatively connected to the cylinder (31).

7. The apparatus for imaging tissues according to claim 6, wherein the locking device (32) comprises:
    an eccentric (33), which eccentric, when in contact with the cylinder (31), forms such a locking device (32) that the eccentric (33) attempts to wedge against a casing of the cylinder (31), when the stretching means (21) being fed between the eccentric and the cylinder is under the influence of a force acting counter to the feeding direction of the stretching means.

8. The apparatus for imaging tissues according to claim 7, wherein the means for locking the stretching means (21) comprises:
a spring (34) for facilitating the engagement of the means for locking, said spring (34) being structured and arranged to press the eccentric against a cylinder (31).

9. The apparatus for imaging tissues according to claim 1, further comprising:
means to operate the traction or transportation means in both a pulling direction of the stretching means (21) as well as in an opposite direction.

10. The apparatus for imaging tissues according to claim 8, further comprising:
a release bar (36), or a corresponding equipment, for releasing the locking of the stretching device (30), said release bar being structured and arranged to contact the eccentric (33) in such a way that when the cylinder (31) is rotated against the feed direction of the stretching means (21) the cylinder turns the eccentric (33) such that the eccentric (33) breaks off contact with the surface of the cylinder (31).

11. The apparatus for imaging tissues according to claim 1, further comprising:
implements to convey the stretching means (21) through the stretching device (30).

12. The apparatus for imaging tissues according to claim 1, further comprising:
sensor means structured and arranged to ascertain if the stretching means (21) has been fed in the stretching device (30).

13. The apparatus for imaging tissues according to claim 12, further comprising:
a control system which has a signal route from the sensor means to the traction or transportation means in order to transmit the information of the reception of the stretching means (21).

14. The apparatus for imaging tissues according to claim 13, further comprising:
means to lock or engage the stretching means (21) to the traction or transportation means based on the identification signal transmitted through the aforementioned signal route.

15. The apparatus for imaging tissues according to claim 4, wherein said means for engaging or locking the stretching means (21) comprise:
an arrangement to drive the traction or transportation means a short distance.

16. The apparatus for imaging tissues according to claim 12, wherein the sensor means comprises:
implements to identify the type of stretching means (21) fed into the receiving means (37), and
implements to control the stretching device (30) on the basis of this identification information.

17. The apparatus for imaging tissues according to claim 1, further comprising:
means for measuring a stretching force exerted on the stretching means (21),
means for measuring a distance that has been pulled,
means for adjusting a traction force, the distance pulled and a traction speed, and
means for setting maximum values for these parameters.

18. The apparatus for imaging tissues according to claim 1, wherein said apparatus has been adjusted, together with a contact or compression device (11, 15, 16) of the tissue to be imaged, to form a positioning device (50) of the tissue to be imaged, whereby the contact or compression device (11, 15, 16) includes one or several contact or compression surfaces (22, 23) approaching the tissue to be imaged, or a contact or compression surface (22, 23) encircling the tissue to be imaged, whereby the stretching means (21) has been arranged to be adjusted between the tissue to be imaged (20) and the contact or compression surface (22, 23) in order to form contact surface or surfaces for the tissue to be imaged (20) and for the stretching implement (21).

19. The apparatus for imaging tissues according to claim 18, wherein the positioning device (50) made up of the stretching device (30) and the contact or compression device (11, 15, 16) further comprises:
means for operating the stretching device (30) and the contact or compression device (11, 15, 16) alternately and/or simultaneously.

20. The apparatus for imaging tissues according to claim 18, wherein in an arrangement with more than one stretching device (30) there are means for at least one of pulling the stretching means (21) for distances of differing lengths on various sides of the tissue and of pulling the tissue from just one side.

21. The apparatus for imaging tissues according to claim 18, wherein the positioning device (50), which is made up of the stretching device (30) and the contact or compression device (11, 15, 16), further comprises:
two stretching devices (30) that have been adjusted in respect of the tissue to be imaged (20), so that the contact surfaces of the stretching means (21) and of the tissue to be imaged (20) are situated on different sides of the tissue to be imaged (20).

22. The apparatus for imaging tissues according to claim 18, wherein said contact or compression device (11, 15, 16) comprises:
connector means for a receiver (14) of the energy form, containing the image information, generated in the imaging process.

23. The apparatus for imaging tissues according to claim 22, wherein the means for attaching the receiver (14) allow for various sized receivers (14), receivers based on different imaging techniques and/or different receiving techniques, to be attached to the contact or compression device.

24. The apparatus for imaging tissues according to claim 22, further comprises:
means for adjusting a distance between an image information receiver (14) and an imaging area.

25. The apparatus for imaging tissues according to claim 18, further comprising:
control means for automatically driving the traction and compression devices on the basis of a pre-determined program based on at least one of thickness and compression force information received from the compression of the tissue to be imaged.

26. A method in tissue imaging, in particular, imaging the tissues of the breast and the breast area, comprising the steps of:
directing an energy emanating from an energy source of an energy form used in the imaging, which energy source is part of an imaging apparatus, to an object to be imaged and further onto a receiver of the form of energy,
containing the image information,
positioning a tissue to be imaged in an imaging area with the help of a contact or compression surface of a positioning apparatus belonging to the imaging apparatus, placing the tissue being imaged into contact with a surface of a stretching means used in a stretching device belonging to the imaging apparatus, to form a contact surface between the tissue being imaged and the stretching device, when the tissue to be imaged is stretched by using the stretching means, which stretching means comprises a layer of flexible material that is translucent to the energy form, containing the image information, used in the imaging, wherein the stretching means has at least one of a rectangular, elongated sheet like, and band like shape, and placing the stretching means in contact with the receiving means belonging to the stretching device, at one end side of the stretching means, or from a corresponding direction in view of the shape of the stretching means.

27. A method according to claim 26, further comprising the step of:

placing the stretching means in contact with a traction or transportation means of the stretching device belonging to the imaging apparatus, and one of:

locking the stretching means into fixed contact with the traction or transportation means at said one side of said stretching means which was fed into the stretching device, and engaging the stretching means to the traction or transportation means at the side adjacent to the side which was fed into the stretching device.

28. A method according to claim 27, wherein the locking or engaging is achieved by driving the stretching means a short distance into the traction device.

29. A method according to claim 26, further comprising the step of:

driving the stretching means around a drum, cylinder, bar, pipe, axle or the like which belongs to the traction or transportation means.

30. A method according to claim 26, further comprising the step of:

identifying the stretching means as being fed into the traction device with the help of the identification means that constitute a part of the traction device.

31. A method according to claim 30, wherein the identification means sends an identification signal to a control system of the imaging apparatus.

32. A method according to claim 31, wherein the control system sends a signal to the traction or transportation device of the stretching means, whereupon the control system locks or engages the stretching means to the traction or transportation device.

33. A method according to claim 26, further comprising the steps of:

identifying, with the help of the identification means, the type of the stretching means fed into the receiving means and controlling the stretching device based on this identification information.

34. A method according to claim 26, wherein the stretching device is driven both in a pulling direction and in an opposite direction of the stretching means.

35. A method according to claim 26, wherein the stretching means is driven through the stretching device.

36. A method according to claim 26, wherein the stretching means is driven out of the imaging apparatus via a different route than it was fed into the imaging apparatus.

37. A method according to claim 26, further comprising the step of:

utilizing more than one contact or compression surface approaching the tissue or a contact or compression surface completely encircling the tissue to be imaged, in order to position the tissue to be imaged, when the stretching means is placed in between one or more of these surfaces and the tissue to be imaged before said surfaces come into contact with each other.

38. A method according to claim 37, wherein the tissue to be imaged is stretched only at one point or at different points at differing lengths.

39. A method according to claim 37, wherein the tissue to be imaged is stretched symmetrically from different sides.

40. A method according to claim 37, further comprising the step of:

simultaneously compressing and stretching the tissue to be imaged.

41. A method according to claim 37, further comprising the step of:

compressing and stretching the object to be imaged several times, before imaging and/or between different imaging operations.

42. A method according to claim 37, further comprising the step of:

taking an image of the same tissue from two or several different angles, while between the previous and the next image the stretching means is driven back to the starting position of the imaging sequence, to the position where it was after becoming locked or engaged to the traction or transportation means of the stretching device.

43. A method according to claim 26, further comprising the step of:

stretching the tissue during the imaging process.

44. A method according to claim 26, wherein different images are taken of the same tissue by changing the distance between the receiver in relation to the tissue to be imaged.

45. A method according to claim 37, wherein the traction and compression means are driven automatically with the help of control means on the basis of a pre-determined program and/or, for example, on the basis of the information on thickness and compression force received from compression of the tissue to be imaged.

* * * * *